United States Patent [19]

Dekker et al.

[11] Patent Number: 4,876,722

[45] Date of Patent: Oct. 24, 1989

[54] ACTIVE NOISE CONTROL

[75] Inventors: Nicolaas M. J. Dekker; John W. Edwards, both of Pinner; Adrian W. James, London, all of England

[73] Assignee: The General Electric Company, p.l.c., England

[21] Appl. No.: 193,801

[22] Filed: May 13, 1988

[51] Int. Cl.4 ........................ A61F 11/02; H03B 29/00

[52] U.S. Cl. ........................................ 381/71; 381/94

[58] Field of Search .................... 381/71, 73.1, 93, 94, 381/96, 169

[56] References Cited

U.S. PATENT DOCUMENTS

| | | | |
|---|---|---|---|
| 4,122,303 | 10/1978 | Chaplin et al. | 381/71 |
| 4,490,841 | 12/1984 | Chaplin et al. | 381/71 |
| 4,527,282 | 7/1985 | Chaplin et al. | 381/94 |
| 4,566,118 | 1/1986 | Chaplin et al. | 381/71 |
| 4,736,431 | 4/1988 | Allie et al. | 381/71 |

*Primary Examiner*—Jin F. Ng
*Assistant Examiner*—David H. Kim
*Attorney, Agent, or Firm*—Kirschstein, Ottinger, Israel & Schiffmiller

[57] ABSTRACT

An active noise control system for reducing the amount of noise propagated along a duct comprises a microphone mounted in the wall of the duct for detecting the noise, and an active antiphase noise source, such as a loudspeaker, which is mounted substantially in the center of the cross-section of the duct. A control circuit coupled between the microphone and the antiphase noise source includes an integrator having a specific transfer function, which improves the loop gain of the microphone/source loop at low frequencies, and secures stability by altering the phase.

8 Claims, 2 Drawing Sheets

AMPLITUDE-FREQUENCY RESPONSE OF INTEGRATOR CIRCUIT $H(s) = \frac{1}{s\tau+1}$

ACTIVE NOISE CONTROL

BACKGROUND OF THE INVENTION

1. Field of the Invention

This invention relates to active control of noise in ducts.

2. Description of Related Art

The principles of active noise control were established by Paul Lueg in 1936 and basically consist of detecting by a microphone the noise which it is wished to control, and replaying the detected noise in antiphase via a loudspeaker so that the regenerated noise destructively interferes with the source noise. Since that time there has been a great deal of research in the field of active noise control. However, the basic configuration for active noise control in a duct has been the provision of the microphone in the centre of the duct and of the loudspeaker in the duct wall. There are good reasons for this arrangement which will be gone into in greater detail later on in this specification.

However, it has been discovered that this known arrangement has disadvantages when there is a fluid medium flowing through the duct.

SUMMARY OF THE INVENTION

An object of the present invention is to provide an active noise control system which reduces these disadvantages.

According to the present invention there is provided on active noise control system comprising a duct through which noise to be controlled propagates; a microphone located in a wall of said duct, a source of anti-sound mounted substantially in the centre of said duct; and means responsive to the magnitude of the sound received by the microphone for driving the anti-sound source to reduce said magnitude.

The anti-noise source may comprise a loudspeaker mounted within the duct, or may comprise an outlet to which the output of a loudspeaker is piped, the loudspeaker itself being external of the duct.

BRIEF DESCRIPTION OF THE DRAWINGS

An embodiment of the invention will now be described, by way of example, with reference to the accompanying drawings, in which.

DETAILED DESCRIPTION OF THE PREFERRED EMBODIMENT

Figure 1:
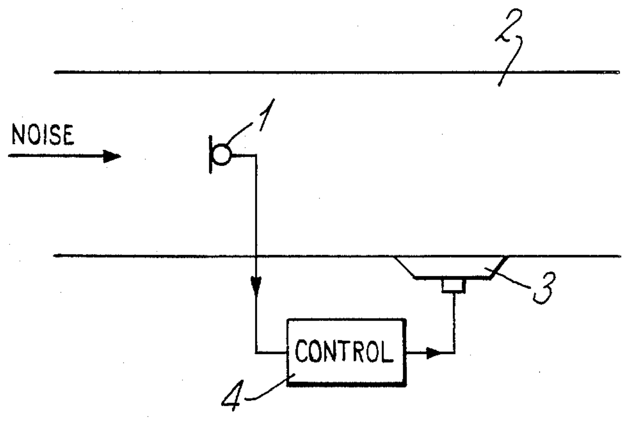
FIG. 1 PRIOR ART
FIG. 1 is a diagrammatic view of a known active noise control system according to the prior art.

Referring now to the drawings, FIG. 1 shows a known arrangement which is essentially that established by Paul Lueg. In this arrangement a sensing microphone 1 is positioned in the centre of a duct 2 and a loudspeaker 3 is located in the duct wall. This is the simplest form of an active attenuator for duct-borne sound. The system includes a controller 4 which includes an electrical signal delay to compensate for the acoustic propagation delay from the sensing microphone 1 to the antisource loudspeaker 3. If the microphone is placed directly in front of the loudspeaker piston, this acoustic delay is eliminated and the controller can be a simple inverting amplifier. Since the microphone senses the sound from the loudspeaker in addition to the primary noise, a closed loop configuration exists and there is a danger of instability. Substantial noise attenuation can be obtained provided the loop gain is high, but stability criteria limit this. In ducts, the positions of the sensor and the loudspeaker are important for stability and maximum obtainable attenuation, as will be shown in the following paragraph.

Figure 3:
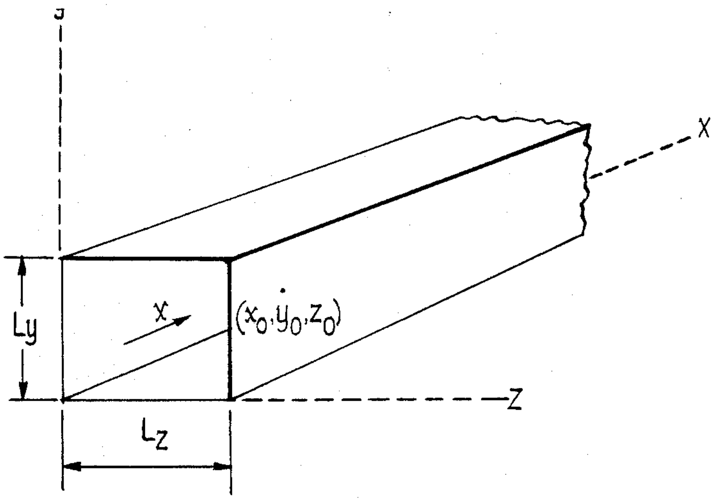
FIG. 3 is a perspective view of a duct.

This can be appreciated by considering the duct shown in FIG. 3. A guided propagated wave in this rectangular duct can be described by equation (1):

$$p(x,y,z,t)=Re.Be^{-j\omega t}.e^{jb_nx}.\Psi_n(y,z) \quad (1)$$

where p is the acoustic pressure $\Psi_n B$ is the pressure amplitude $$b_n = \sqrt{k^2 - a_n^2}$$

$k$ = the wave number $$a_n = \pi^2\left[\left(\frac{n_y}{L_y}\right)^2 + \left(\frac{n_z}{L_z}\right)^2\right] \quad (2)$$

$$\psi_n(y,z) = D(n_y,n_z)\cdot\cos\frac{n_y\cdot\pi\cdot y}{L_y}\cdot\cos\frac{n_z\cdot\pi\cdot z}{L_z} \quad (3)$$

with the constant $D(n_y,n_z)$ determined from the identity for the orthogonality of eigenfunctions:

$$1/A\int\int\Psi_n(y,z).\Psi_{n'}(y,z)dA=\delta_{nn'}$$

where A is the duct cross-sectional area.

A microphone placed in this duct will sense the pressure as described in equation (1) and measures both plane and transverse waves. The latter cannot be cancelled with a simple monopole antisource and the contribution of these waves to the total pressure, and consequently to the overall loop gain, does not contribute to the cancellation of plane waves. The phase shift caused by these transverse modes, especially at resonance frequencies, is also detrimental to the noise reduction which is obtainable. This is due to the reduction in the open loop gain necessary to maintain stability. It can be shown, however, that the ratio between total acoustic pressure and pressure due to plane waves is minimal when the microphone is placed in the duct centre. If the loudspeaker is mounted in the duct wall, as in FIG. 1, most transverse modes can be generated in addition to the plane wave mode, and the plane waves and even-numbered ($n_y$ and $n_z$ are even numbers) transverse modes are sensed by the centre mounted microphone. Positioning the microphone in the centre of the duct has, however, the disadvantage that airflow in the duct causes turbulence at the microphone resulting in a locally generated noise field. This gives rise to the electrical output of the microphone no longer being directly related to the acoustic field propagating down the duct. This severely restricts the obtainable attenuation and some form of microphone wind screening is essential.

Figure 2:
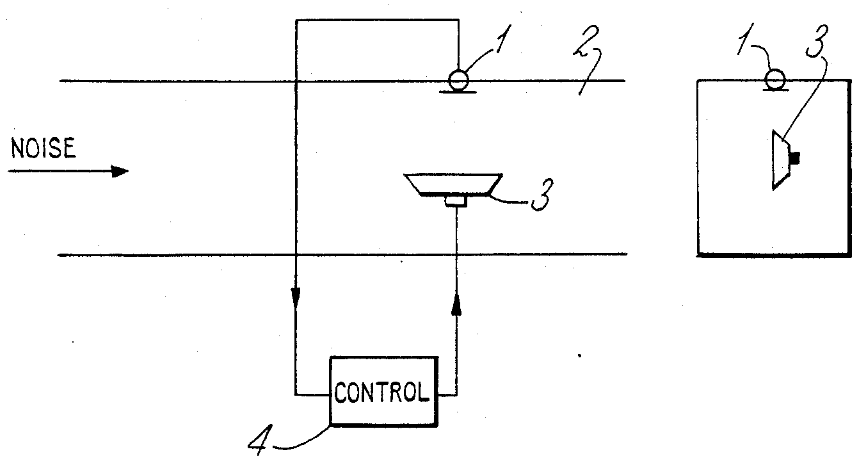
FIG. 2 is a similar view of a system according to the present invention.

Accordingly the present invention proposes that the microphone should be incorporated in and located flush with the surface of the duct wall, as is shown in FIG. 2 of the accompanying drawings. In this position the microphone no longer generates any flow noise because the air flow velocity at the duct surface is zero. However, there is limitation of attenuation because the microphone is no longer at a position where the contribution of transverse modes to the total acoustic pressure is minimal.

This problem can be alleviated by placing the antisource loudspeaker in the centre of a transverse cross-section of the duct. In this way a minimum number of transverse modes are generated. Thus if a point source $(x_o, Y_o, z_o)$ is placed in a duct the pressure amplitude can be written as $$p(x,y,z) = \Sigma_n X_n(x) \cdot \psi_n(y,z) \qquad (4)$$

$$\text{where } X_n(x) = \frac{-2\pi S \cdot \psi_n(y_o,z_o)}{jAb_n} \cdot e^{jbn|x|}$$

with $\hat{S}$ the monopole pressure amplitude. From equation (3) it can be shown that $$y_o = \frac{L_y}{2} \text{ and } z_o = \frac{L_z}{2} \text{ then } \psi_n(y_o,z_o)$$

is nonzero only if $n_y$ and $n_z$ are even integers. Hence, only one quarter of all transverse waves will be generated.

It has been found that an active noise control system with the configuration of a wall-mounted microphone and a centre-placed antisource yields satisfactory attenuation when there is airflow in the duct.

It will be appreciated that an antisource placed in the duct rather than in the duct wall will generally occupy a larger volume than a microphone and will therefore provide a larger obstruction to the airflow. In most practical applications, however, the active system will be integrated with a passive absorber, such as a splitter silencer. In such a case there would not be a significant increase in the overall air resistance.

Another important consideration is system stability. The active noise control system operates in a closed loop configuration due to the acoustic signal path from the loudspeaker back to the sensing microphone, and consequently the system could become unstable. To prevent this, stability criteria must be met and gain and phase need to be controlled. Since the amplitude-frequency response of a loudspeaker rolls off a low frequencies (i.e. a decreasing output with decreasing frequency), the open loop gain in this frequency region will decrease as well. The effect on the closed loop transfer function is that the loop phase goes through zero, which could lead to instability.

Figure 5:
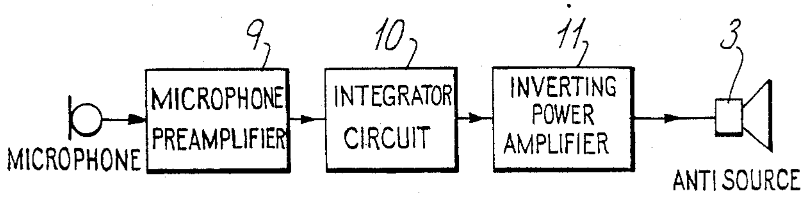
FIG. 5 is a block diagram of a control circuit.

To meet this problem the system according to the invention incorporates an integration circuit. This is shown at 10 in FIG. 5 from which figure it can be seen that the control circuitry leading from microphone 1 to loudspeaker 3 comprises a microphone preamplifier 9, the integrator 10 and an inverting power amplifier 11. The inverting amplifier 11 provides the necessary phase shift to ensure that the output of the loudspeaker 3 interferes destructively with the noise detected by the microphone 1.

Figure 4:
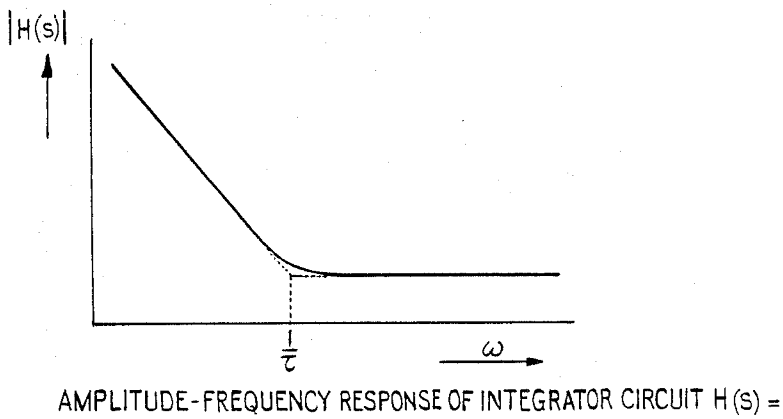
FIG. 4 is a response graph.

The integrator circuit 10 is intended not only to improve the loop gain at low frequencies thereby increasing the achievable attenuation, but also to modify the phase shift around the loop to secure operational stability. The integrator circuit 10 has therefore been given the amplitude-frequency response shown in the graph of FIG. 4. To produce this response the circuit 10 has a transfer function $$H(s) = \frac{1}{s\tau + 1}$$

where $s = j.\omega$, $j = \sqrt{-1}$, $\omega$ is the frequency in rads and $\tau$ the circuit time constant. High frequency stability can be ensured by reduction of gain by means of passive absorptive material placed on the walls of the duct.

We claim:

1. An active noise control system for reducing the amount of noise propagated through a duct, comprising: a microphone incorporated in a wall of said duct, and operative for detecting the sound of the propagated noise; a source of anti-sound mounted substantially at the center of a transverse cross-section of said duct; and a control circuit responsive to the magnitude of the sound detected by the microphone for driving the anti-sound source to substantially suppress first transverse mode excitation in said duct.

2. A system as claimed in claim 1, wherein said anti-sound source comprises a loudspeaker.

3. A system as claimed in claim 1, wherein said control circuit includes integrating circuit means for improving loop gain and aiding stability of a loop comprising said microphone and said anti-sound source by changing the phase of a microphone signal output.

4. A system as claimed in claim 3, wherein said control circuit further comprises microphone preamplifier means coupled between said microphone and said integrating circuit means, and inverting power amplifier means coupled between said integrating circuit means and said anti-sound source.

5. A system as claimed in claim 4, wherein said integrating circuit means has a transfer function H(S) which is equal to $1/s\tau+1$, where $s=j\omega$ where j is $\sqrt{-1}$, $\omega$ is the frequency in rads and $\tau$ the circuit time constant.

6. A system as claimed in claim 5, wherein passive absorptive material is disposed at the inner surface of the walls of said duct.

7. An active noise control system for reducing noise propagated along a duct through which a fluid medium flows, comprising:

(a) a microphone for detecting the propagated noise;

(b) means for mounting the microphone in and flush with a wall of the duct at a substantially calm location where the fluid medium flows at a virtually zero velocity;

(c) anti-sound means for radiating sound in an anti-phase relationship with the noise detected by the microphone;

(d) means for mounting the anti-sound means substantially at the center of a transverse cross-section of the duct of minimize transverse mode excitation within the duct; and (e) control means operatively connected to the microphone and the anti-sound means, and operative for driving the anti-sound means in response to the noise detected by the microphone to radiate sound which destructively interferes with the propagated noise.

8. A system as claimed in claim 7, wherein the control means includes an integrator having an amplitude versus frequency transmission characteristic wherein low frequencies are attenuated to a greater extent than high frequencies.

* * * * *